United States Patent [19]

Monkman et al.

[11] Patent Number: 5,536,473
[45] Date of Patent: Jul. 16, 1996

[54] POLYANILINE GAS SENSOR

[75] Inventors: Andrew P. Monkman, Stanhope; Michael C. Petty, Stockton-on-Tees; Napoleon E. Agbor, Durham; Margaret T. Scully, Raynes Park, all of United Kingdom

[73] Assignee: British Gas plc, London, United Kingdom

[21] Appl. No.: 284,436

[22] PCT Filed: Jan. 13, 1994

[86] PCT No.: PCT/GB94/00075

§ 371 Date: Sep. 6, 1994

§ 102(e) Date: Sep. 6, 1994

[87] PCT Pub. No.: WO94/16316

PCT Pub. Date: Jul. 21, 1994

[30]  Foreign Application Priority Data

Jan. 13, 1993 [GB]  United Kingdom ............ 9300560

[51]  Int. Cl.⁶ .......................................... G01N 7/00
[52]  U.S. Cl. .................. 422/90; 422/98; 422/83; 436/106; 436/116; 436/118
[58]  Field of Search .................. 422/90, 9.8, 83; 436/106, 116, 118

[56]  References Cited

U.S. PATENT DOCUMENTS

| | | | |
|---|---|---|---|
| 4,025,704 | 5/1977 | Trevoy | 526/16 |
| 4,226,692 | 10/1980 | Isenberg | 204/195 S |
| 4,338,281 | 7/1982 | Treitinger et al. | 422/98 |
| 4,569,826 | 2/1986 | Shiratori et al. | 422/90 |
| 4,940,640 | 7/1990 | MacDiarmid | 429/213 |
| 4,984,446 | 1/1991 | Yagawara et al. | 73/31.06 |
| 5,079,334 | 1/1992 | Epstein et al. | 528/210 |
| 5,109,070 | 4/1992 | Epstein et al. | 525/189 |
| 5,159,031 | 10/1992 | Epstein et al. | 525/540 |
| 5,164,465 | 11/1992 | Epstein et al. | 525/540 |
| 5,208,301 | 5/1993 | Epstein et al. | 525/540 |
| 5,250,170 | 10/1993 | Yagawara et al. | 204/431 |

Primary Examiner—Jill Warden
Assistant Examiner—Sharidan Carrillo
Attorney, Agent, or Firm—Oblon, Spivak, McClelland, Maier & Neustadt

[57]  ABSTRACT

A gas sensor for use in monitoring gases such as $H_2S$, $NO_2$ or $SO_2$ comprises a film or layer of non-protonated polyaniline as the gas sensing material.

3 Claims, 19 Drawing Sheets

FIG. 18

| GAS | CONC. (ppm) in $N_2$ | DELAY TIME $\tau$ (s) | RECOVERY TIME (MINS) | EXPOSURE TIME (MINS) | MINIMUM DETECTION (ppm) | NORMALIZED CHANGE $\Delta R/R/ppm$ |
|---|---|---|---|---|---|---|
| $NO_x$ | 10 | 48 | 28 | 6 | 4 | -0.026 |
| $H_2S$ | 10 | 36 | 56 | 4 | 3 | -0.033 |
| $SO_2$ | 10 | 12 | 110 | 6 | 2 | -0.036 |
| CO | 10000 | NO MEASURABLE EFFECT | N/A | 25 | N/A | N/A |
| $CH_4$ | 50000 | NO MEASURABLE EFFECT | N/A | 25 | N/A | N/A |

| GAS | CONC. (ppm) in $N_2$ | DELAY TIME $\tau$ (s) | RECOVERY TIME (MINS) | EXPOSURE TIME (MINS) | MINIMUM DETECTION (ppm) | NORMALIZED CHANGE $\Delta R/R$/ppm |
|---|---|---|---|---|---|---|
| $NO_x$ | 10 | <10 | 54 | 6 | 2 | -0.02 |
| $H_2S$ | 10 | 144 | 120 | 12 | 6 | 0.02 |
| $SO_2$ | 50 | 30 | <90 | 12 | 1 | $-3.4*10^{-3}$ |
| CO | 10000 | NO MEASURABLE EFFECT | N/A | 50 | N/A | N/A |
| $CH_4$ | 50000 | NO MEASURABLE EFFECT | N/A | 50 | N/A | N/A |

| GAS | CONC. (ppm) in $N_2$ | DELAY TIME $\tau$ (s) | RECOVERY TIME (MINS) | EXPOSURE TIME (MINS) | MINIMUM DETECTION (ppm) | NORMALIZED CHANGE $\Delta R/R/ppm$ |
|---|---|---|---|---|---|---|
| $NO_x$ | 100 | 72 | <120 | 24 | 20 | $-1.6*10^{-3}$ |
| $H_2S$ | 100 | 131 | <90 | 6 | 5 | -0.011 |
| $SO_2$ | 1000 | NO MEASURABLE EFFECT | N/A | 6 | N/A | N/A |
| CO | 10000 | NO MEASURABLE EFFECT | N/A | N/A | N/A | N/A |
| CH | 50000 | NO MEASURABLE EFFECT | N/A | N/A | N/A | N/A |

POLYANILINE GAS SENSOR

BACKGROUND OF THE INVENTION

The present inventions relates to gas sensors and to methods of making them.

Applicants are particularly, though not exclusively, interested in gas sensors for use in monitoring gases, such as acid gases, e.g. $H_2S$, $NO_2$ and $SO_2$, in connection for example with industrial process control or environmental protection.

It is well known that organic polymers may form the gas sensing material in gas sensors. Such organic materials include conducting polymers which are normally p-type semiconductors whose conductivities are changed when exposed to oxidising gases such as $NO_x$ or reducing gases such as $NH_3$. Sensors using such materials have been based on both electrical techniques and optical techniques (e.g. surface plasmon resonance).

Various organic polymers, such as polyaniline, which appear to be suitable as gas sensing materials are commonly deliberately 'doped' to improve the specificivity and/or sensitivity of the materials towards particular gases. Such 'doping' also increases the electrical conductivity and facilitates the detection of change in conductivity of the polymer on exposure to and interaction with the gases being sensed; the change in conductivity being used as a measure of the concentration of the sensed gases.

With some organic polymers, such as polyaniline, in order for doping to be achieved the cationic part of the dopant can only be a hydrogen ion. In such a case the doped form of the polymer can be regarded as the protonated form.

SUMMARY OF THE INVENTION

Applicants investigations have revealed that there is a disadvantage with gas sensors comprising such protonated polymers as the sensing material. Applicants have found that the protonated polymers are unstable as gas sensing materials in the sense that they have a tendency to produce inconsistent conductivity readings; thus unreliable results may be obtained. It is believed that this disadvantage is a consequence of the mechanism of the interaction between the gases being sensed and the polymer which involves a direct de-doping or de-protonating process resulting in undesired degradation of the material.

An object of the invention is to overcome or alleviate the disadvantages associated with protonated polymeric materials as mentioned above.

Accordingly, the present invention provides a gas sensor comprising a film or layer of non-protonated polyaniline as the gas sensing material.

In this specification the term "non-protonated" means that less than 1% of the protenatable imine nitrogen in the polyaniline is protonated.

The non-protonated polyaniline may be in the base (neutral) emeraldine form as depicted by the formula:

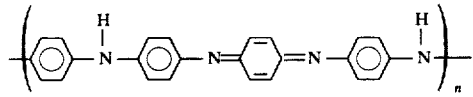

or may be in the base (neutral) leuco-emeraldine form (that is the fully reduced form), as depicted by the formula:

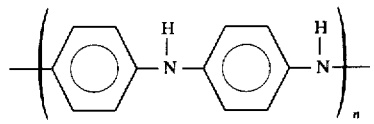

Alternatively, the non-protonated polyaniline may be formed of a mixture of base emeraldine and base leuco-emeraldine forms.

The base emeraldine form appears to be stable up to about 200° C. in air while the base leuco-emeraldine form appears to be stable up to about 200° C. in an inert atmosphere such as argon or nitrogen.

According to another aspect of the invention a method of making non-protonated polyaniline comprises treating protonated polyaniline with an alkaline solution to de-protonate the material.

The alkaline solution may be an ammonium hydroxide solution.

It will be appreciated that the non-protonated material should not be contacted with a proton-donating species, such as an inorganic acid before being incorporated into a gas sensor.

Dry, solid non-protonated material may be obtained by separating the material from the alkaline solution, for example by filtering, washing the filter cake with water, and optionally in addition with an organic solvent such as isopropanol, after which the filter cake may be suitably dried, for example under vacuum at room temperature.

The dried non-protonated material may be stored in a dry inert atmosphere, for example in a vacuum desiccator.

Where the gas sensor is based on an electrical technique, the film or layer of non-protonated polyaniline may conveniently be deposited on a substrate already supporting spaced electrodes, so that the deposited film or layer bridges the spaced electrodes. For example, the substrate may have thereon a pair of interdigitated electrodes.

The thickness of the film or layer may be from about 5 nanometers to about 5 micrometers.

The substrate may be any suitable insulating, inert material such as the material forming a printed circuit board or glass or quartz.

The electrodes may be made of any suitable inert conductor, such as gold, platinum, or gold-plated copper.

Various methods or techniques may be used to deposit the film or layer on the substrate. For example, in one method the polyaniline may be dissolved in a suitable solvent, such as N-methyl-2-pyrrolidinone (NMP), to produce a solution, for example of 0.01 to 10% wt/wt concentration, from which the film or layer may be cast or spun onto the substrate. In one such a method it is preferred to subject the solution to centrifuging which, in effect, serves as a spin filtration step which filters out undissolved particles of polyaniline, before 'spreading' a film on a horizontally disposed substrate employing a spinning operation. In the spinning operation a predetermined amount of the solution is deposited on the substrate which is supported on a horizontal spinning surface arranged to spin about a vertical axis. Initially the spinning surface is slowly accelerated to a relatively slow speed which is maintained for a period to distribute the polyaniline over the substrate, after which the speed is increased to a maximum in order to produce a substantially uniform thin film.

In another method the polyaniline may be deposited by vacuum evaporation or sublimation onto the substrate in accordance with procedures generally known per se. In a further method the polyaniline film or layer may be formed by using Langmuir-Blodgett techniques generally known per se.

BRIEF DESCRIPTION OF THE DRAWINGS

In order that the invention may be more readily understood reference will now be made, by way of example, to the accompanying drawings, in which:

FIGS. 18 and 19 show the effect of different gases on polyaniline films at room temperature.

FIG. 18 is a summary of the effect of different gases on spin-coated polyaniline at room temperature.

FIG. 19 is a summary of the effect of different gases on evaporated thin film of polyaniline at room temperature.

FIG. 20 is a summary of the effect of different gases on LB film of polyaniline at room temperature.

DESCRIPTION OF CERTAIN PREFERRED EMBODIMENTS

A METHOD OF PREPARING NON-PROTONATED POLYANILINE IN POWDER FORM

Figure 1:
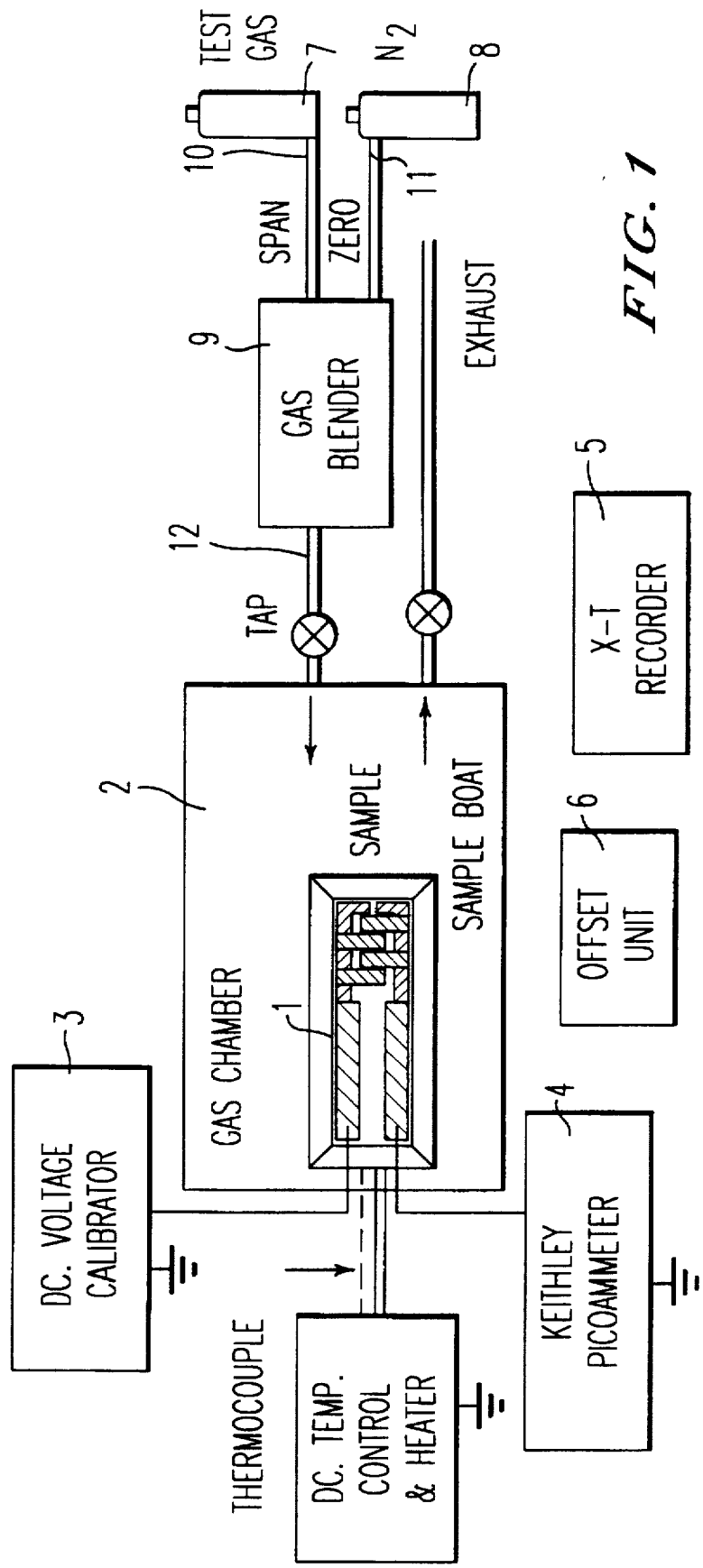
FIG. 1 illustrates in schematic and block diagram form, apparatus for measuring the resistance/conductivity of a film of non-protonated polyaniline deposited on an interdigitated electrode structure to form a gas sensor.

The "emeraldine base" form of polyaniline was prepared as follows. Aniline (0.1 moles) was added to hydrochloric acid solution (100 ml, 3.5%, ca. 0.1 moles HCl) in a 250 ml beaker, and mixed using a magnetic stirrer to give a solution with a final pH between 1 and 2, as measured by indicator paper. Ammonium persulphate (0.1 moles) to act as the oxidising agent to effect polymerisation of the aniline was dissolved in distilled water (60 ml), and this was added to the stirred reaction mixture. The mixture turned a dark blue/green colour and the reaction was observed to be slightly exothermic over a period of about 10 minutes. The mixture was left to stir for a total of about 6 days, after which it was filtered and washed with water, then methanol (to remove any low molecular weight species), and finally with more water. The filter cake was added to an ammonia solution (100 ml, 35%) and stirred for 7 hours before filtering and repeatedly washing with water, occasionally interspersed with washing with isopropanol. At this point the filtrate was colourless, indicating that the filtrate had been washed sufficiently. The filter cake was then dried under vacuum at 20° C. for 24 hours to give a brown/purple product which was crushed using a mortar and pestle. Elemental analysis showed that the material contained small residual amounts of chlorine (0.50 wt %) and sulphur (0.38 wt %). 4.69 wt % was not accounted for and, inventors believe, is ascribed to oxygen, possibly associated with the chlorine or sulphur, or with trapped solvent species (water, methanol, or isopropanol). Isopropanol was subsequently positively identified in $^{13}C$ spectra. Chlorine and sulphur residues are normally found in the products of such preparations and they remain largely unchanged by attempts to wash them out suggesting that they may be present as ring substituents.

PREPARATION OF THE GAS SENSOR

Example 1—using spin-coating to form a thin film of non-protonated polyaniline.

Polyaniline powder obtained from the above described method of preparation was dissolved in N-methyl-2-pyrrolidinone (NMP) at 20° C. in an amount to produce a 5% (by wt.) solution (blue in colour) of polyaniline.

The solubility of the polyaniline in the solvent was found to improve with time and after 48 hours the solution was further prepared (prior to forming a thin layer on the electrode structure) in either of the two following ways:

1. By centrifuging the solution and then decanting, Applicants obtained satisfactory results by repeating these operations several times, for example three times, with the centrifuge operating each time at a speed of about 4000 rpm for a period of about 30 minutes.

By homogenising the solution, for example at a speed of about 20500 rpm for about 10 minutes.

The centrifuging process is used, in effect, as a filtration like step to remove relatively larger particles/aggregates from the solution whilst the homogenising process is used to break up and disperse the relatively larger particles/aggregates in the solution.

Samples from the resulting centrifuged or homogenised solution are then used in a spin-coating operation which deposits or forms a thin film of the polyaniline on the surface of the cleaned electrode structure.

Spin-coating techniques are known per se and in the present operation the parameters were controlled so that the resulting thin film on the electrode structure had a substantially constant thickness of, for example, about 1 micrometer (μm) (±0.01 μm).

In the spin-coating operations conducted by the inventors it was possible to program specific spinning conditions into the spinner control apparatus in relation to the initial acceleration phase, the constant speed spinning periods and the deceleration phase so that duration times, spinning speeds and ramp were controlled.

As an example, the inventors found that the following spinning conditions involving essentially four steps produced satisfactory films:

(i) The spinner surface supporting the cleaned electrode substrate structure was accelerated from zero in a few seconds to 520 rpm which was maintained for 60 secs to distribute the polyaniline over the electrode structure.

(ii) At the end of the 60 secs at 520 rpm, the speed was accelerated to 1500 rpm (within a few tenths of a second) which was maintained for 60 secs in order to produce the thin film of substantially uniform thickness.

(iii) At the end of the 60 secs at 1500 rpm, the spinner was decelerated to 300 rpm (within a few tenths of a second) which was maintained for 20 secs to aid solvent removal so that the film does not shrink before it is 'dry'.

(iv) At the end of the 20 secs at 300 rpm, the spinner was decelerated to zero speed (within a few tenths of a second).

Thus the spinning operation only a little over 2 minutes 20 seconds.

The inventors found that high quality films could be reproducibly formed using the above described procedure. The quality of the films was judged using optical microscopy, with high quality films being considered to be ones which were not only of substantially uniform thickness but were relatively free from 'pin-holes'.

The interdigitated electrode structure comprised a pair of gold-plated copper electrodes which had been photolithographically developed onto a substrate of printed circuit board or glass. Each electrode had 32 digits or fingers. The overlap distance of the electrode digits or fingers was about 14.3 mm whilst the finger width had spacing was about 0.381 mm.

The electrode structure now carrying the thin film was then heated in a vacuum oven at about $10^{-2}$ mbar to a temperature of 120° C. for 10 minutes to remove NMP solvent from the film substantially completely.

Both uncoated and coated electrode structures were subjected to experiments involving the recording of current passed therethrough against applied voltage at room temperature (20° C.) in the dark by using the apparatus as shown in FIG. 1.

Gas sensing measurements were performed on the gas sensor structure by exposing the sensor to different gases (diluted in $N_2$) in a chamber through which the gases were passed—as will be described below. (The gases were all obtained from British Oxygen Company—Special Gases Division with purities up to 99% and were introduced into the chamber via a Signal Instrument Series 850 gas blender).

With the object of producing thin films of the polyaniline for analysis purposes, the thin films were produced by spinning the polyaniline onto glass substrates at a speed of about 3000 rpm for 30 seconds using solutions of the polyaniline powder (as prepared above) dissolved in NMP as solvent, in solvent:solute weight ratios of 10:1, 100:1 and 1000:1. In each case the solutions obtained were dark blue indicating that the polyaniline is in a non-protonated form.

Protonated polyaniline does not dissolve in the NMP solvent to any significant extent unless specific surfactant counter ion acids are used to protonate the material.

Again the thin films, this time supported by the glass substrates, were transferred to a vacuum oven and heated at $10^{-2}$ mbar to a temperature of 120° C. for 10 minutes.

The thickness of the thin films of polyaniline formed by the spinning process on the glass substrates was found to be of the order of 0.1 μm as measured using a surface profiling Talystep.

Figure 2:
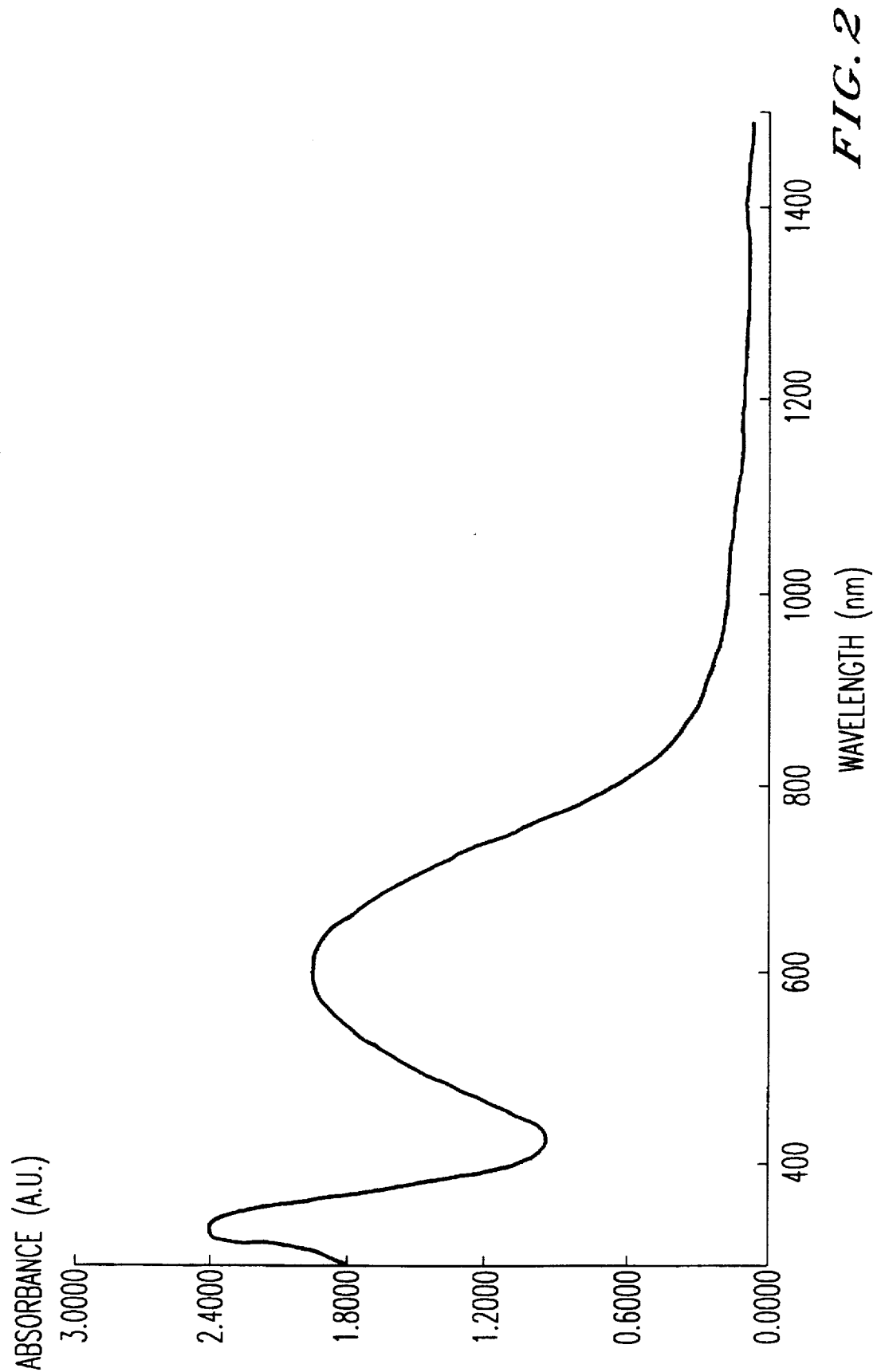
FIG. 2 is an ultra-violet/visible absorption spectrum of non-protonated emeraldine base form of polyaniline which the inventors made and heat treated at 120° C. for ten minutes in vacuum.

FIG. 2 is a representative example of the UV-VIS spectrum of the heat treated polyaniline film, obtained using a Perkin-Elmer Lambda 19 spectrophotometer. Two adsorption bands are clearly evident at about 320 nm and 635 nm and these are considered to be characteristic of the non-protonated emeraldine base form of polyaniline.

The inventors interpret the above findings as confirmation that no significant thermally induced chemical degradation took place during the vacuum heating process to remove solvent.

Example 2— using an evaporation deposition method for forming a thin film of non-protonated polyaniline.

An evaporation method carried out in a vacuum chamber was used to produce a thin film of non-protonated polyaniline in the base leuco-emeraldine form on a substrate such as a glass substrate or on an electrode structure located in the chamber. Incorporated into the system was a temperature controller which maintained a substantially constant source temperature, an adjustable shutter to control the deposition/growth time and a mask to define the specific area of deposition. Initially a source boat or container, located within the chamber but separated from the substrate, was heated up to 300° C. to drive off surface contamination. 40 mg of non-protonated polyaniline powder obtained from the earlier described method were then introduced into the source boat and the system was evacuated to a background pressure of $10^{-3}$ mbar. With the shutter closed, the temperature was raised to and maintained at 400° C. by means of a heater. When a stable pressure was reached, the shutter was opened and evaporated polyaniline was thereby allowed to pass into the region containing the substrate and to deposit through the mask onto the substrate. The deposition was allowed to proceed for a predetermined or fixed length of time for control purposes. After such deposition, the system was allowed to cool to room temperature and return to ambient pressure, and the substrate bearing the deposited film removed. A typical thickness of the deposited film obtained by the above described method was found to be about 120 nm for a shutter time of 30 min.

Example 3—using a Langmuir-Blodgett method for forming a thin film of non-protonated polyaniline.

PREPARATION OF A SOLUTION OF THE POLYANILINE

Using non-protonated polyaniline obtained from the earlier described method, a solution of the polyaniline for use in LB film deposition was prepared by first making a mixture of 1:10 by weight of acetic acid:polyaniline (as an aid to spreading). The acid was completely absorbed by the polymer and no change in colour from the dark blue of the polyaniline was observed. 0.1 mg of the mixture was then dissolved into 10 ml of solvent and sonicated for 30 minutes. The solvent used was a mixture of chloroform:n-methyl-2 pyrrolidinone in a 1:5 weight ratio.

LB FILM FORMATION

The non-protonated polyaniline solution was added to a tank of water and the solution was found to spread uniformly on the water surface without any visible sign of aggregation. The surface pressure versus area isotherm at 20°±2° C. after multiple (~4) compressions revealed the material to form a reasonably condensed layer up to 40 mNm$^{-1}$ surface pressure. On the assumption that the area per molecule of the acetic acid was negligible, the area per emeraldine base repeat was 0.20 nm$^2$ at 30 mNm$^{-1}$ surface pressure. It was thus concluded that the polymer did not form a monomolecular film on the water surface. The floating film was stable for several hours at a surface pressure of 30 mNm$^{-1}$. The substrate on which the film was to be formed was dipped into the floating film at speeds of 2 mmmin$^{-1}$, allowing at least 20 minutes between the first and second dips. Z-type deposition with a transfer ratio of 1.0±0.1 on all dip cycles was observed. The films formed on the substrates were reasonably uniform, by visual inspection, for up to 50 layers.

By way of illustration, the 10:1 sample which produced, via the spin-coat method, good quality films was used to form the thin film on the electrode structure.

With reference to the apparatus in FIG. 1, a sample of the electrode structure bearing the thin film of non-protonated polyaniline 1 is held in the dark and at constant temperature (20° C.) in a sample chamber 2. A voltage is applied to the electrode structure via a D.C. voltage calibrator 3 (in effect, a constant voltage source) while current through the film is monitored via the picoammeter 4. A voltage output is derived from the picoammeter 4. A voltage output is derived from the picoammeter and applied to the y-axis of a y-t chart recorder 5. Thus the chart recorder will reflect change in current through the film (and thus the resistance/conductance) as a function of time. An offset unit 6 allows a constant voltage to be added (in parallel with the output from the picoammeter) in order to 'back-off' the output of the picoammeter and allow small current changes to be monitored.

A test gas source 7 and a dilution gas source 8 (nitrogen in present experiments) are connected to a gas blender 9 via respective inlets 10 and 11. An outlet 12 from blender 9 is connected to the sample chamber for introducing the blended gases into the chamber 2.

Figure 3:
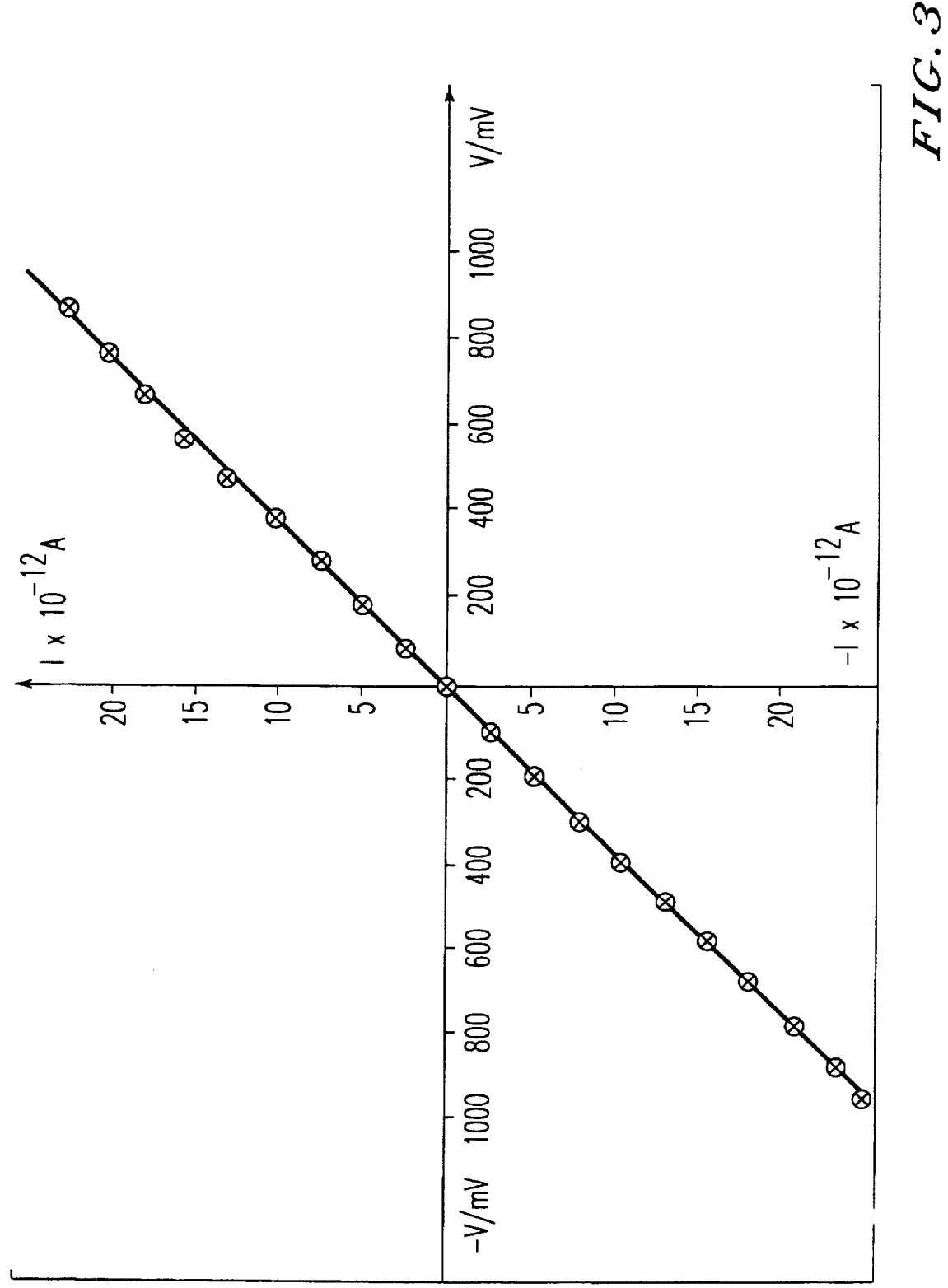
FIG. 3 shows a current against voltage characteristic of the non-protonated emeraldine base form of polyaniline in air at room temperature when using gold-plated copper interdigitated electrodes.

FIG. 3 shows good linearity of the current versus voltage characteristic in respect of the thin film of polyaniline on the interdigitated electrode structure as a result of experiments conducted in air at room temperature (20° C.). Experiments conducted on the uncoated electrode structure produced results (not shown) that confirmed that in the case of the coated electrode structure substantially all of the current which was flowing across the structure was flowing through the polyaniline film rather than the substrate. The good linearity of the current versus voltage characteristic and the increase in slope of the line observed by the inventors for thicker films (data not shown) indicate that ohmic contacts were established between the electrodes and the polymer film.

The conductivity of the sample was calculated to be 1.5×10$^{-11}$ Scm$^{-1}$ which was a good comparison with a literature value of 1×10$^{-11}$ Scm$^{-1}$.

Figure 4:
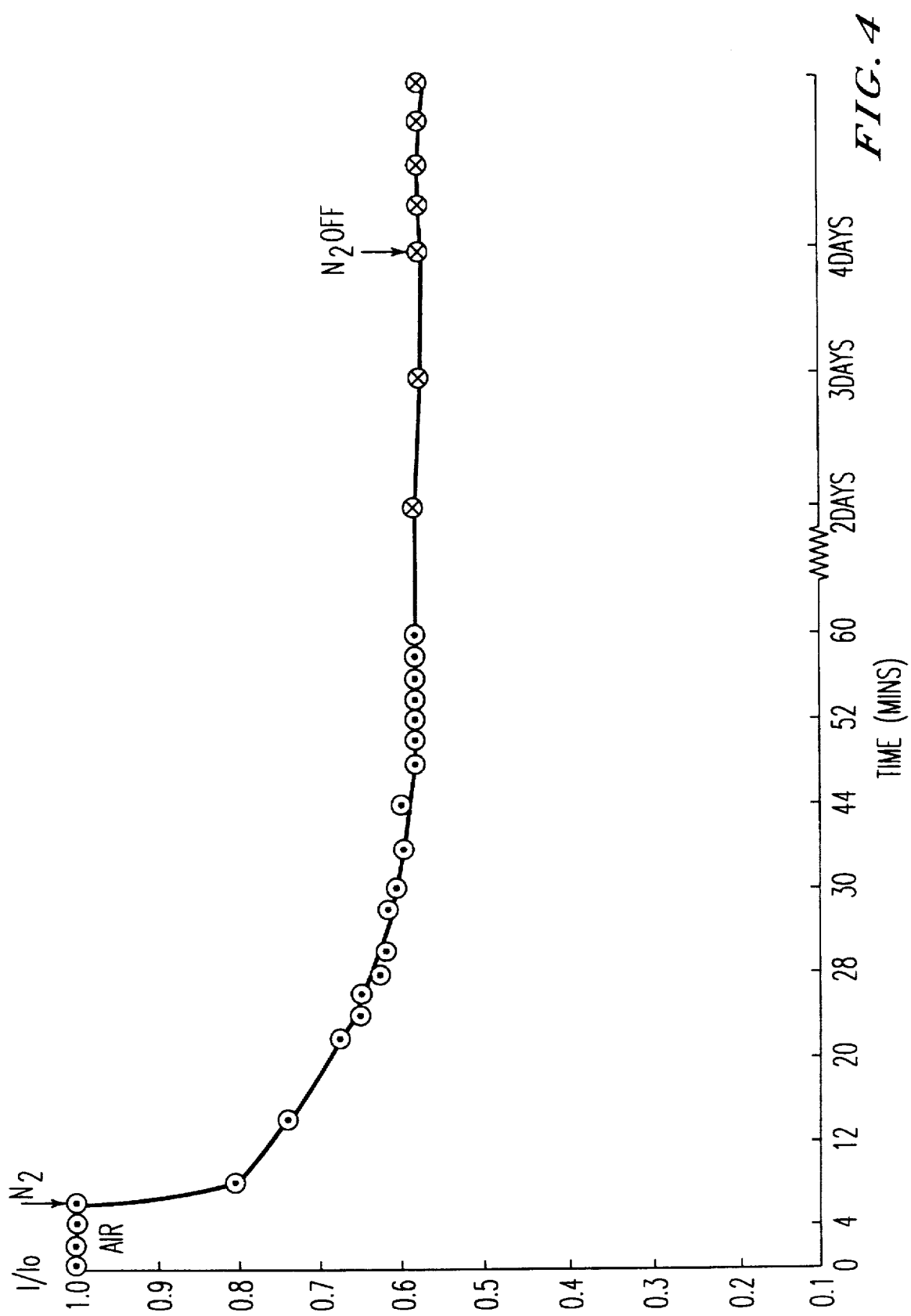
FIG. 4 illustrates the effect that the presence of $N_2$ on non-protonated emeraldine base form of polyaniline has on the conductance of the film.

The conductivity was found to be relatively stable in air but on exposure to a flow of nitrogen gas in the sample chamber it decreased, rapidly at first, over a period of minutes to a lower stable value. Such a change is shown in FIG. 4 in a case where 200 mV was applied across the electrode structure. The change in conductivity is attributed to the removal of water molecules trapped in the polymer matrix. The final stable conductivity in N$_2$ was considered to provide a good baseline for the gas sensing experiments.

Gas sensing measurements were carried out at room temperature (i.e. 20° C.) using test gases diluted in nitrogen, as mentioned above. For each experiment the polyaniline coated electrode structure served as a chemiresistor and the effect of exposing the chemiresistor to the different gas was studied. In separate experiments, each test gas (diluted with N$_2$) was introduced into the sample chamber, so as to be in contact with the polyaniline film, for a specific length of time which was chosen having regard to the sensitivity of the device to the particular test gas.

The test gases used were NO$_x$, H$_2$S, SO$_2$, CO and CH$_4$. On exposure of the polyaniline film to any of the gases NO$_x$, H$_2$S and SO$_2$ a substantial increase in current flow through the film, and thus an increase in conductivity, was observed. In contrast, on exposure of the film to CO or CH$_4$ no measurable change in the conductivity was observed.

Figure 5:
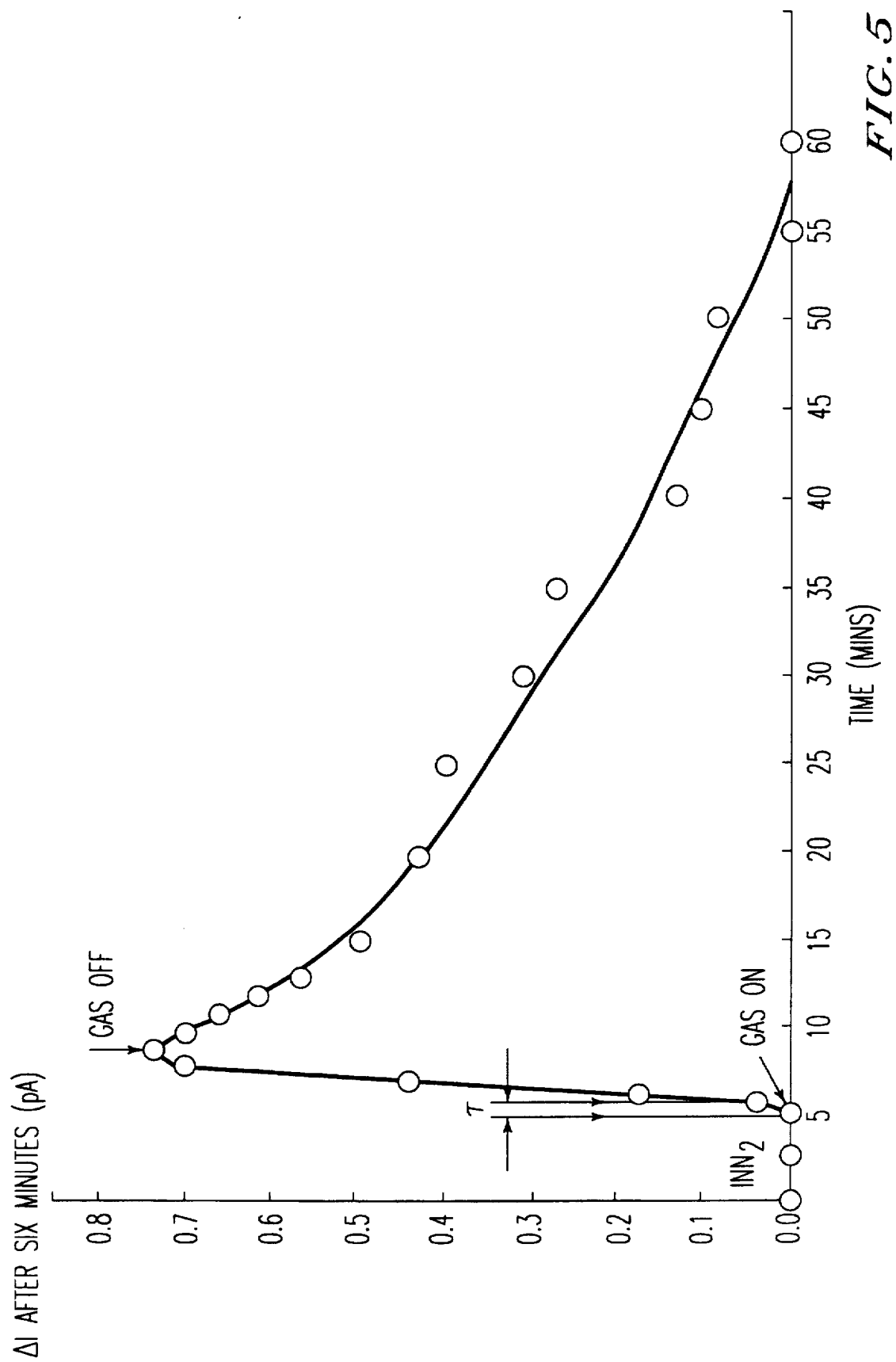
FIG. 5 shows the conductivity response curve of the sensor when the non-protonated polyaniline film is exposed to 8 ppm of $H_2S$ at room temperature.

FIG. 5 shows a typical response of the sensor when exposed to 8 ppm of H$_2$S. The response was found to be reversible with a short delay time. In FIG. 5, τ represents the delay time, i.e. the time between turning 'on' the test gas and the first measurable change in current through the polyaniline film sensor. This delay time includes the time taken for the test gas to flow from its source through connecting pipework to the sample chamber and the time to interact with, and cause a resistance change in, the film. Thus, although in FIG. 5 the delay time is shown as approximately 30 seconds, the actual response of the sensor will be much less.

Figure 6:
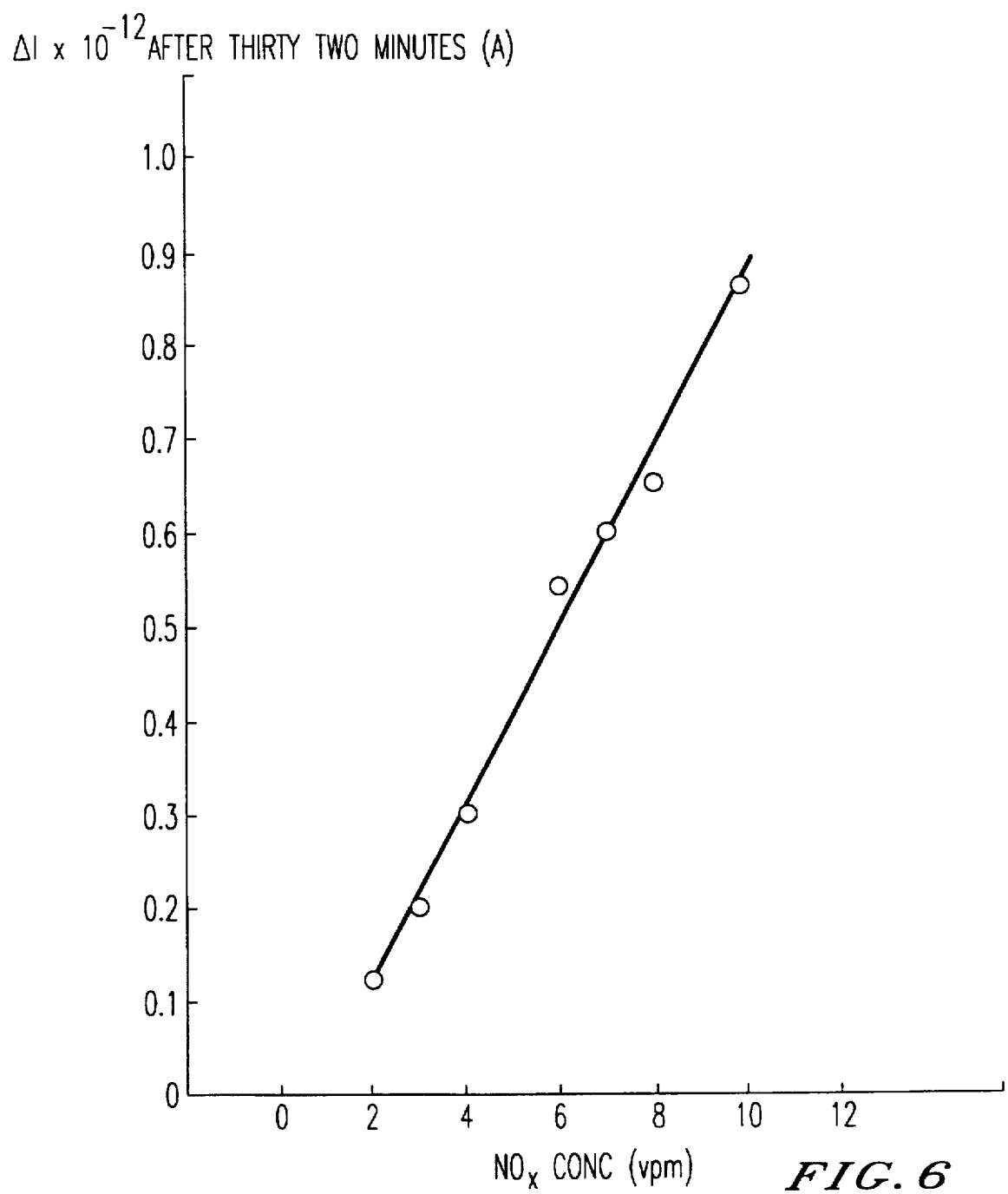
FIGS. 6, 7 and 8 illustrate how the conductivity changes in a film of non-protonated polyaniline in the base emeraldine form (obtained by spin-coating) on exposure at room temperature to different concentrations of $NO_x$ (i.e. $NO_2O_4$ etc.), $SO_2$ and $H_2S$, respectively.
Figure 7:
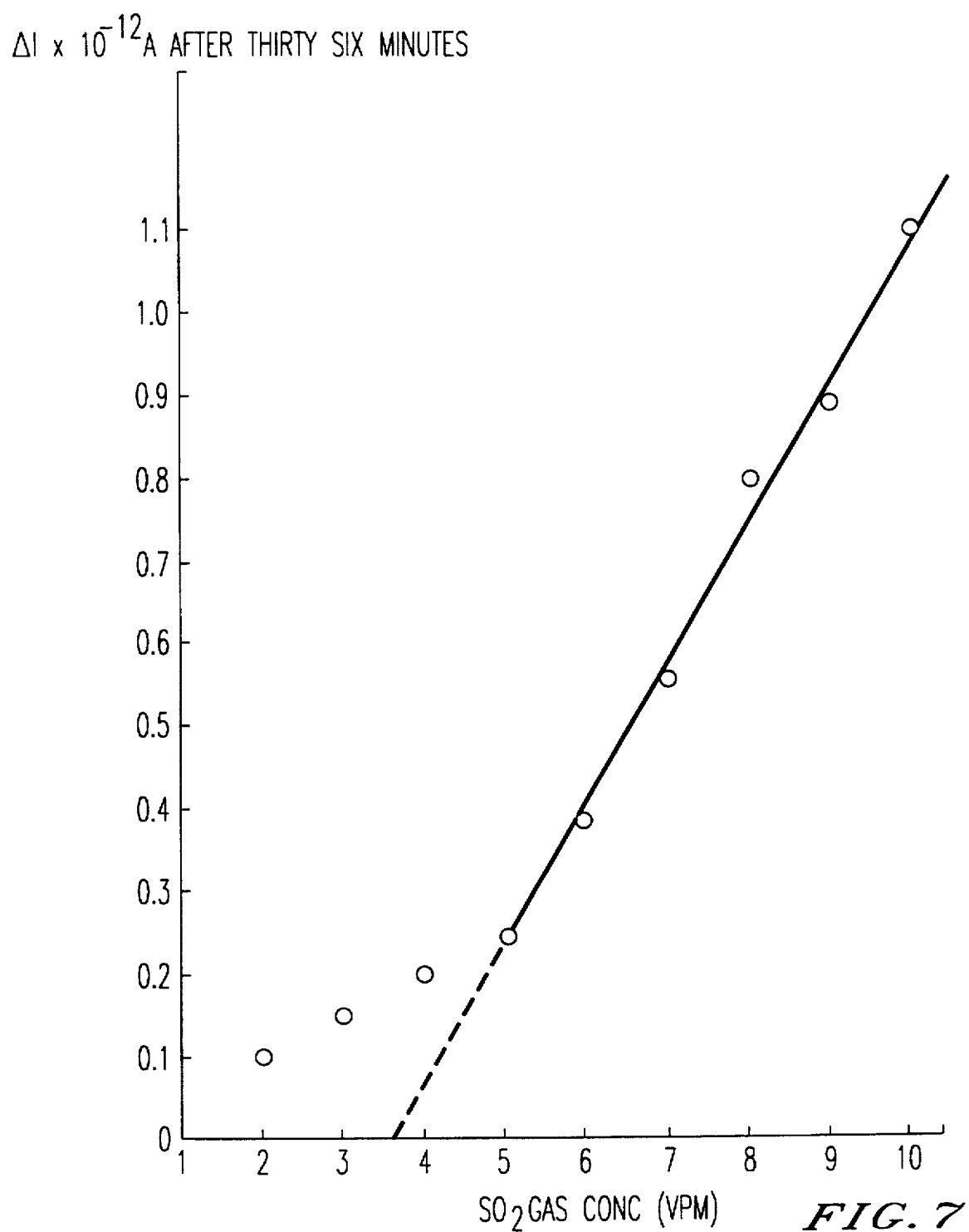
Figure 8:
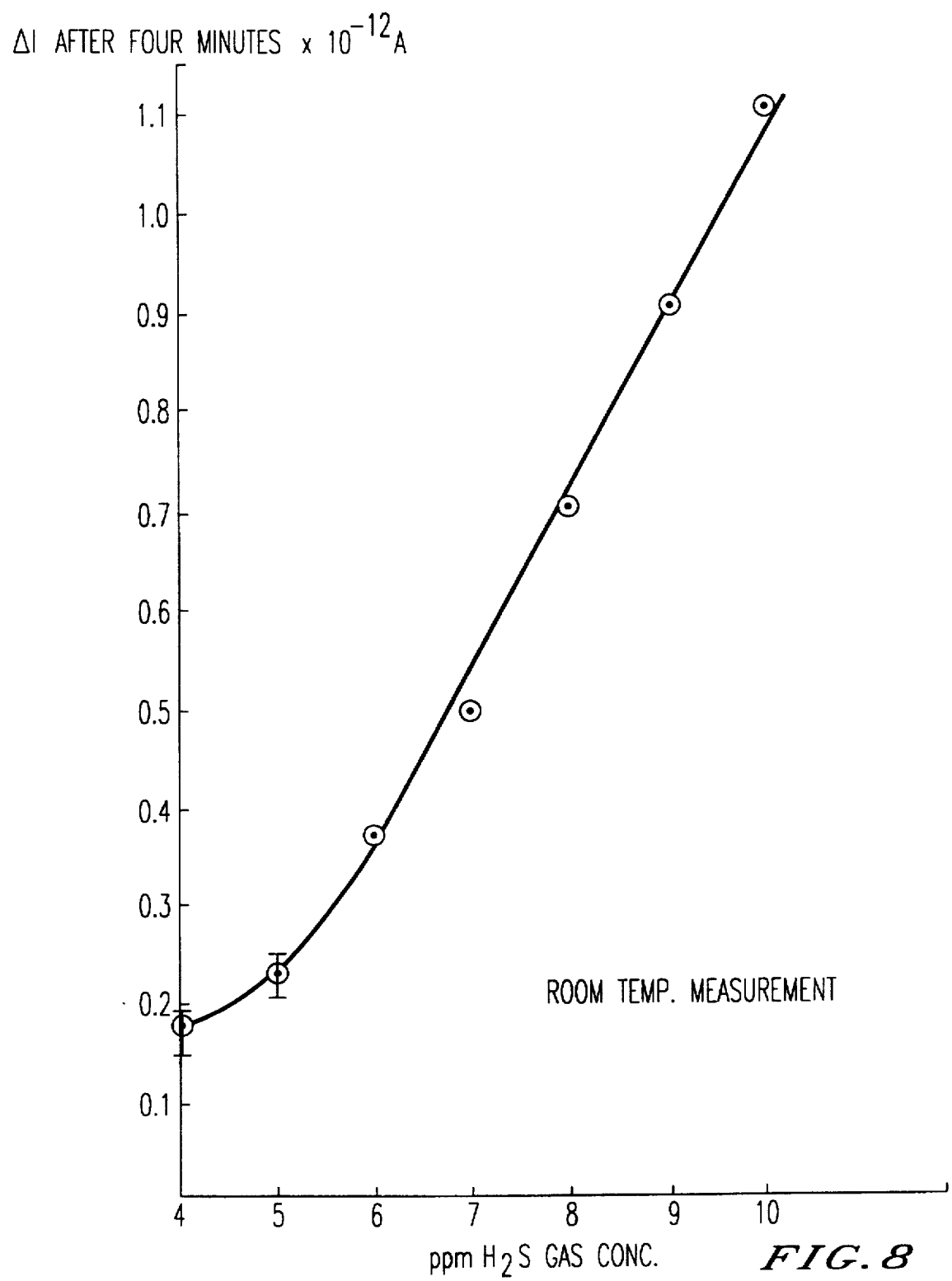

Conductivity measurements which resulted by exposing non-protonated base emeraldine form (obtained using the spin-coating method), when used as the gas sensing material, to different concentrations of NO$_x$, SO$_2$ and H$_2$S are shown respectively in FIGS. 6, 7 and 8. It can be seen that H$_2$S has the largest effect on the conductivity across the sensor while NO$_x$ has the smallest effect. Substantially reversible responses were obtained using any of these three gases.

Figure 9:
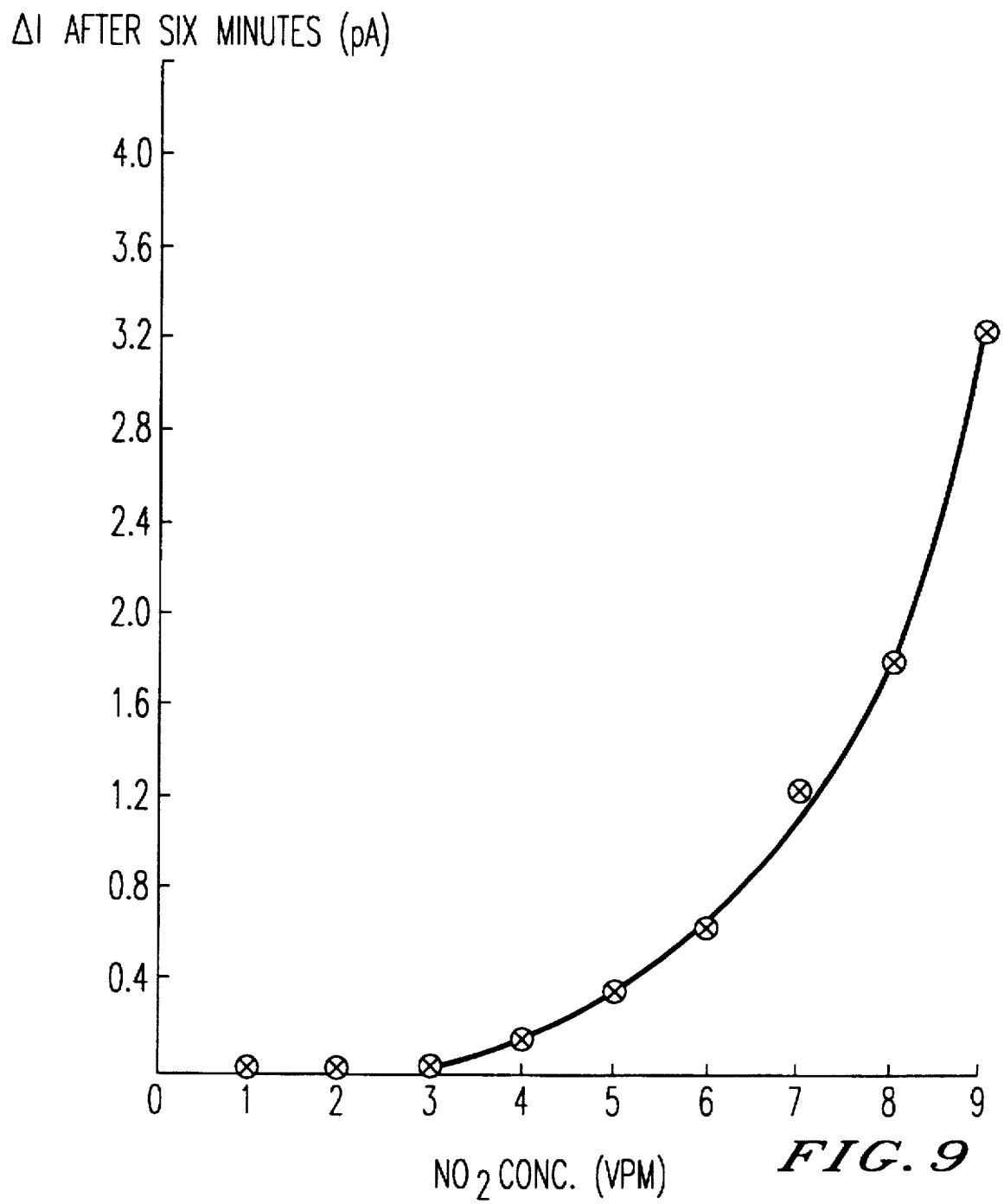
FIGS. 9, 10 and 11 illustrate how the conductivity changes in a film of non-protonated polyaniline in the leucoemeraldine form (obtained by vacuum evaporation) on exposure at room temperature to different concentrations of $NO_2$, $SO_2$ and $H_2S$, respectively.
Figure 10:
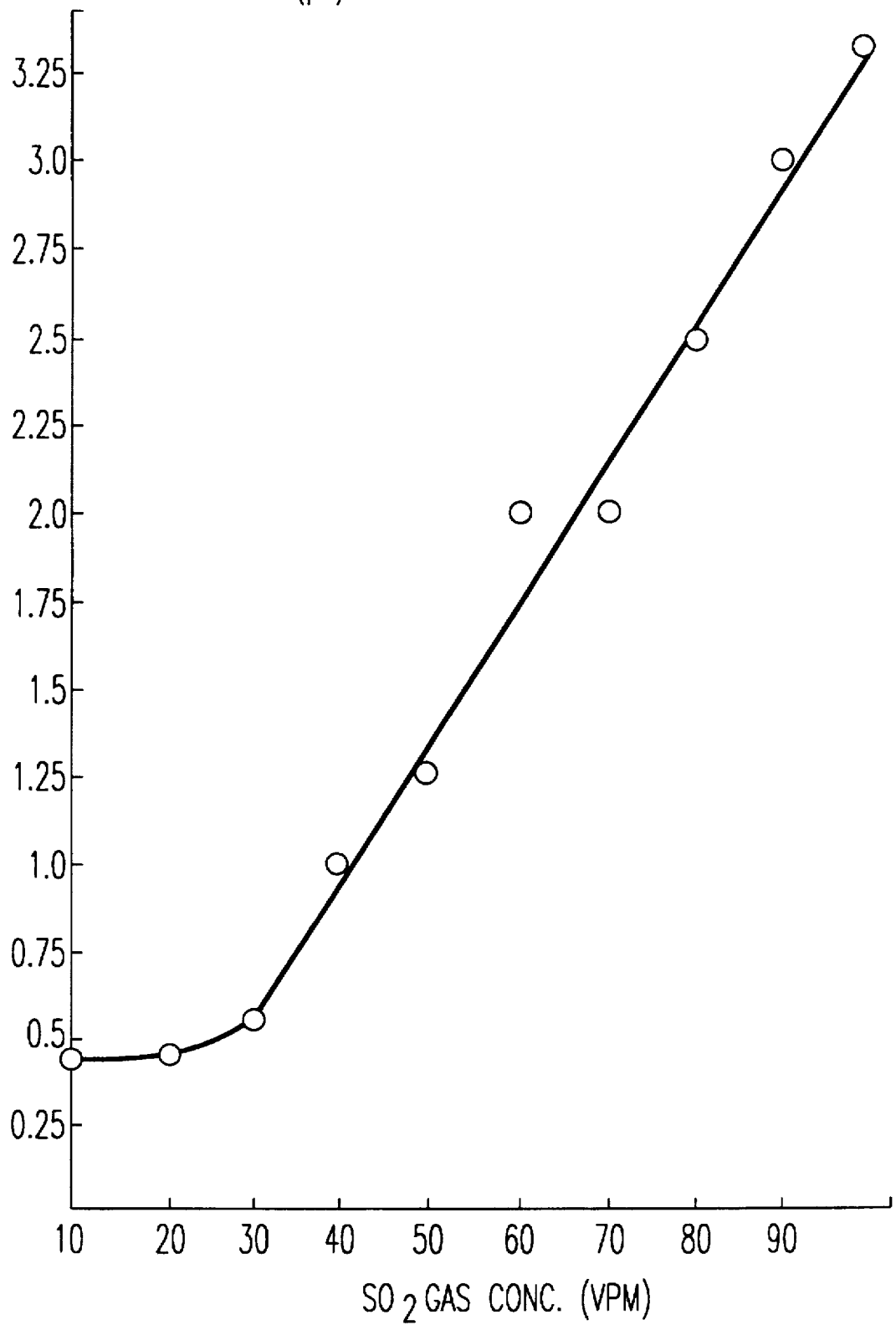
Figure 11:
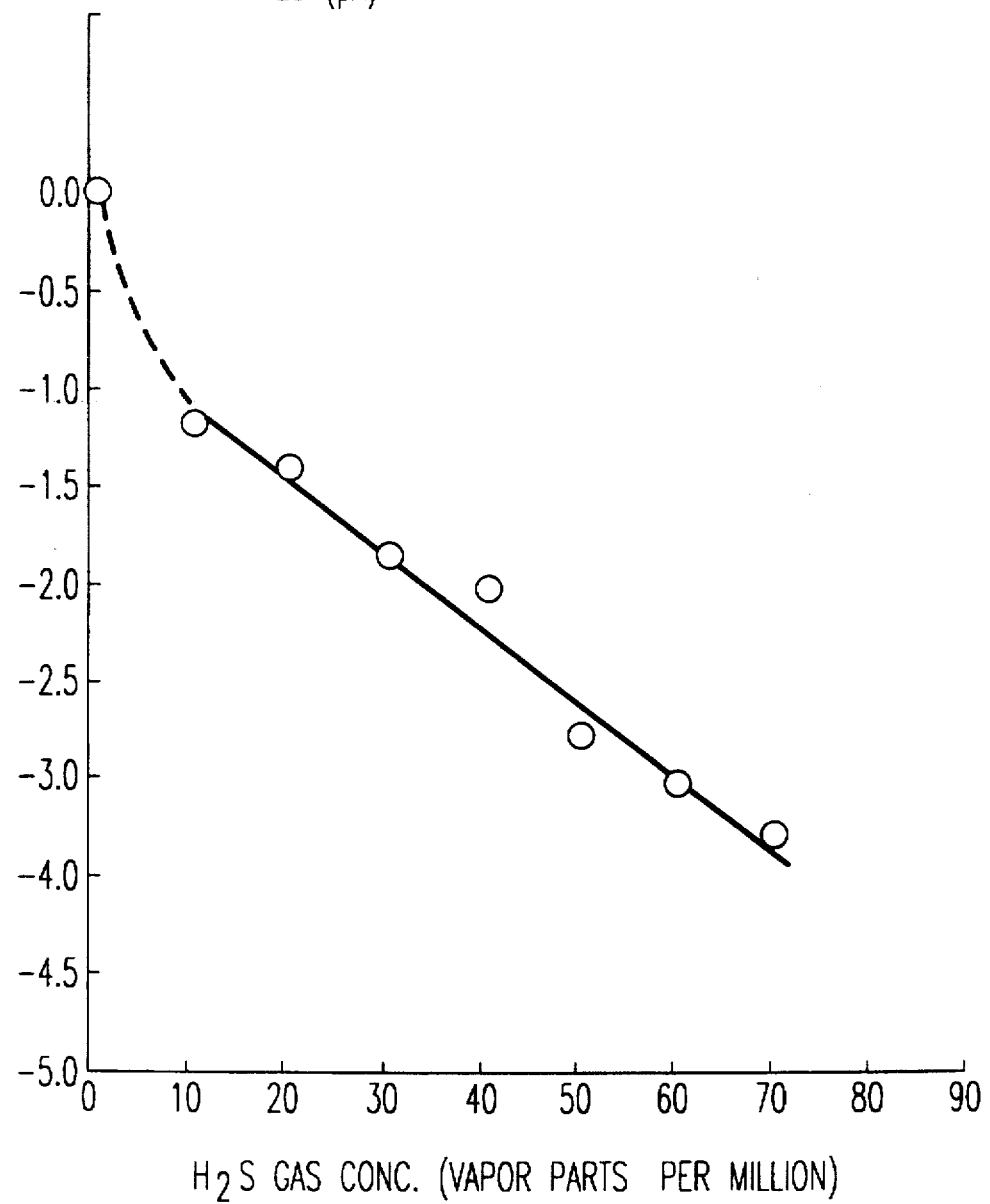

Conductivity results obtained by exposing the non-protonated base leuco-emeraldine form (produced via the vacuum evaporation method), when used as the gas sensing material, to different concentrations of NO$_2$, SO$_2$ and H$_2$S are shown respectively in FIGS. 9, 10 and 11. It will be noted that while this form of the polyaniline was again also sensitive to exposure to the gases, it led to different responses compared with those shown in FIGS. 6, 7 and 8. In particular, with respect to sensing H$_2$S an increase in concentration of the gas led to an increase in current in FIG. 8 but a decrease in current in FIG. 11.

Figure 12:
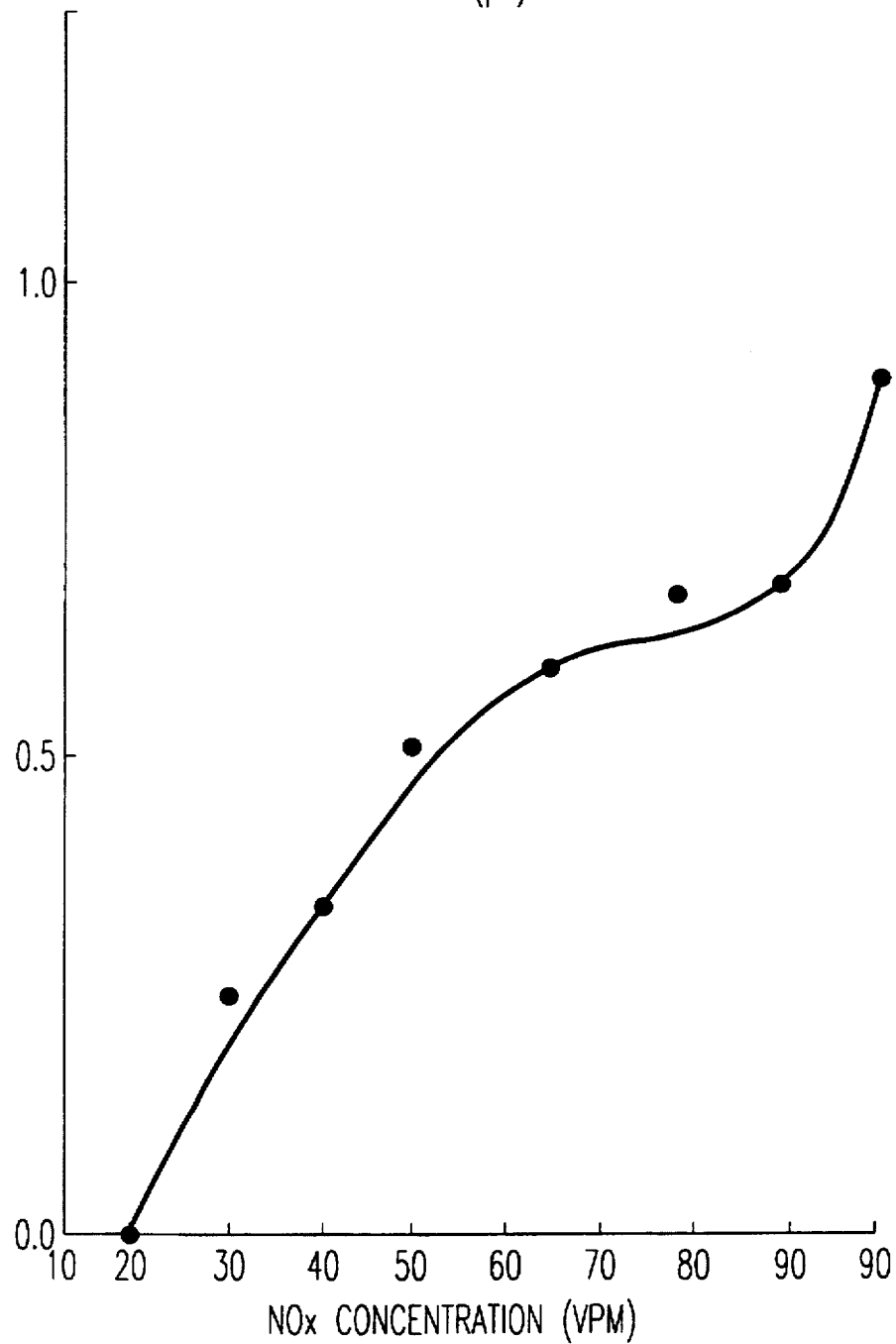
FIGS. 12 and 13 illustrate how the conductivity changes in a film of non-protonated polyaniline in the base emeraldine form (obtained by Langmuir-Blodgett deposition technique) on exposure at room temperature to different concentrations of $NO_x$ and $H_2S$, respectively.
Figure 13:
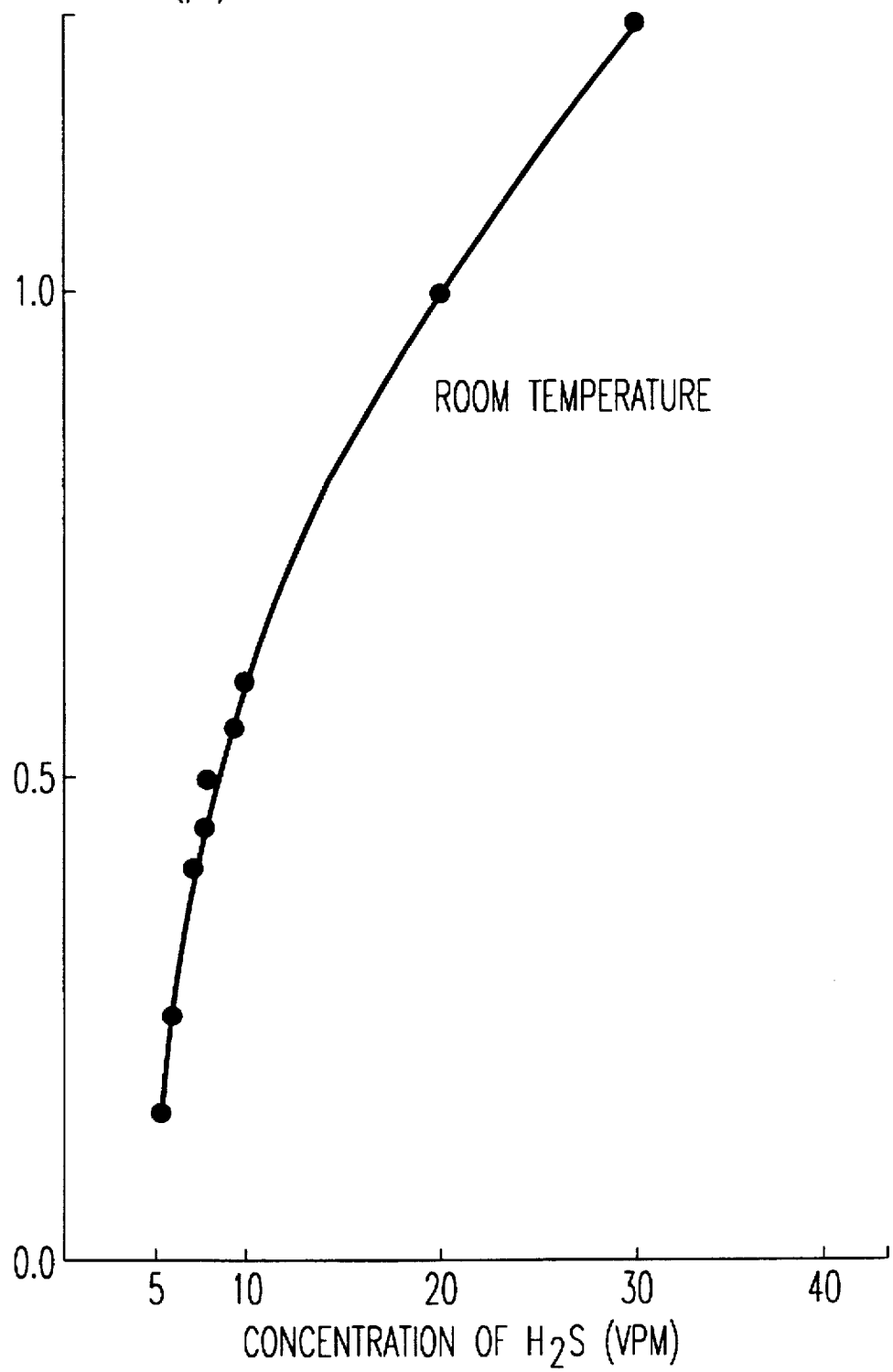

Illustrative conductivity measurements which resulted by exposing non-protonated base emeraldine form (obtained using the Langmuir-Blodgett preparation method), when used as the gas sensing material, to different concentrations of NO$_x$ and H$_2$S are shown respectively in FIGS. 12 and 13. It will be noted that the responses obtained here are different compared with the previously illustrated responses.

Applicants have noted that the three different methods described above for forming the films or layers of the organic polymeric material enable a very wide range of film thicknesses to be obtained and it is envisaged that appreciation of this may enable the sensitivity of the films to particular gases to be optimised.

Illustrations of results obtained from the experiments are summarized in FIGS. 18, 19, and 20. In these Figures, "Normalised change" relates to the sensitivity of the film to the various gases; it is the fractional resistance change ($\Delta R/R$) divided by the gas concentration (ppm). The greater the figure obtained, the more sensitive is the film to the particular gas concerned.

It will be appreciated that by initially employing known concentrations of gases the results can be used to calibrate the gas sensor, such that subsequently when an unknown concentration of gas is used the conductivity measurement can be used as a measure of the gas concentration.

The results obtained from the above described experiments indicated that non-protonated polyaniline, as opposed to protonated forms of polyaniline is stable at room temperature and with respect to the flow of gas thereover, and can be used as a selective, reproducible and reversible sensing material in a gas sensor for sensing the presence of e.g. $H_2S$, $NO_x$ and $SO_2$ in very low concentrations (down to a few parts per million) at room temperature. The selectivity to different gases can be determined by the different values or the slope of the response curve.

Figure 14:
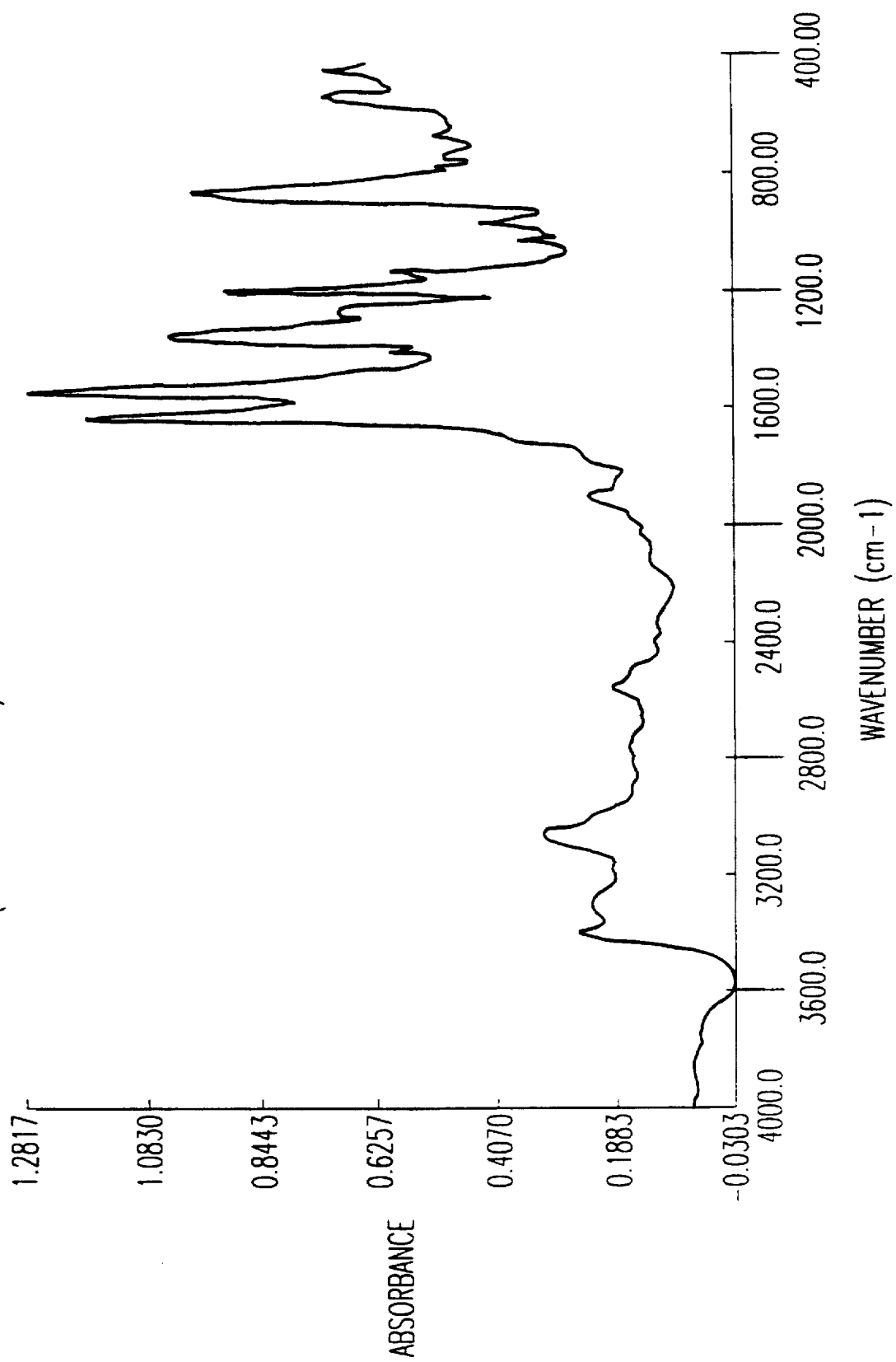
FIG. 14 is an infra-red absorption spectrum of a sample of non-protonated emeraldine base form of polyaniline made by the inventors.
Figure 15:
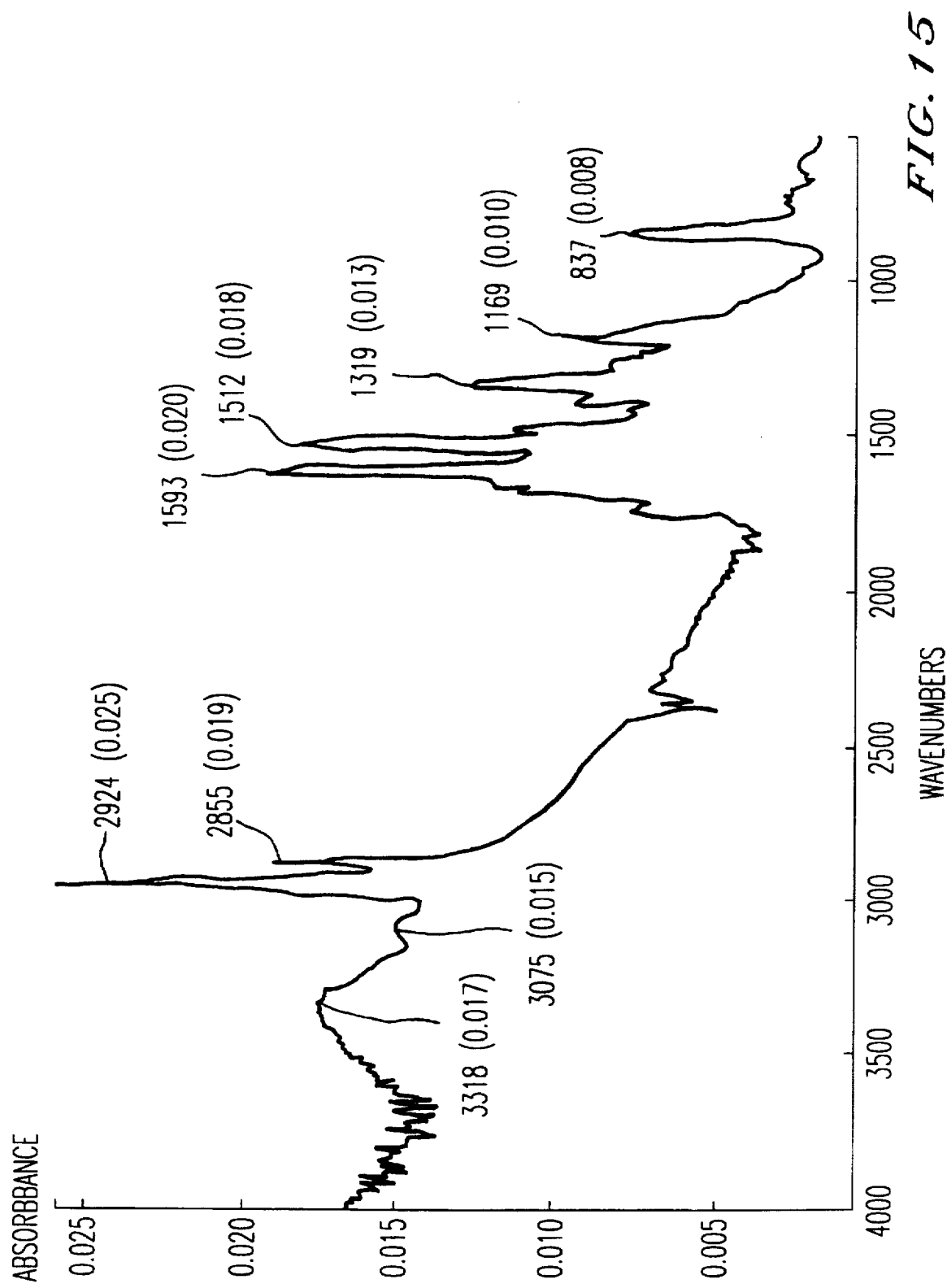
FIG. 15 is an infra-red absorption spectrum of a sample of slightly protonated form of polyaniline.
Figure 16:
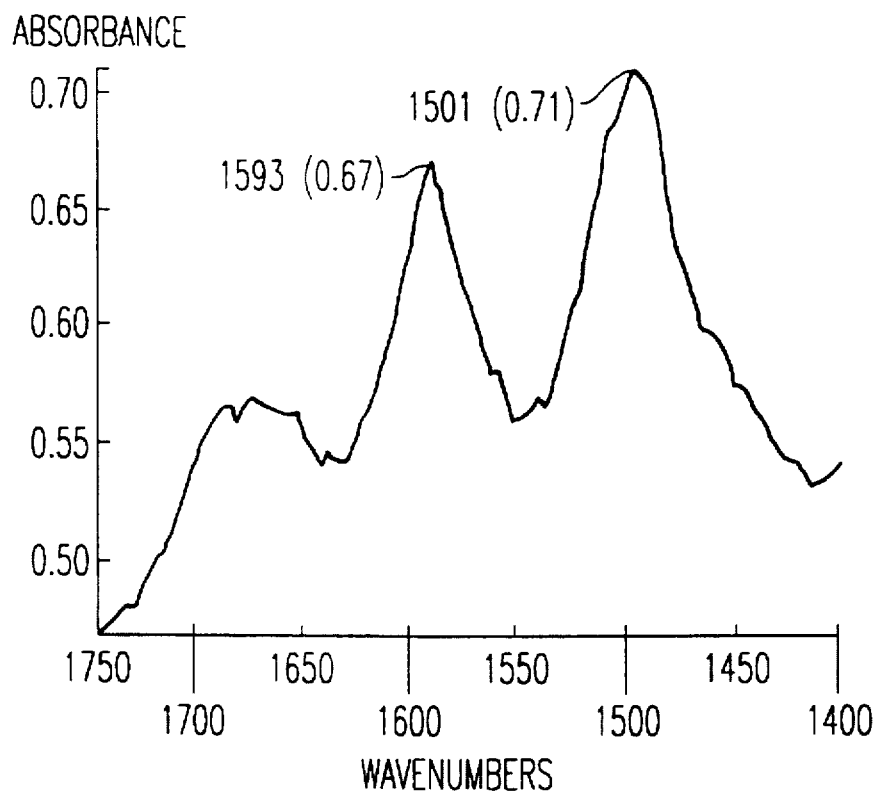
FIGS. 16 and 17 show on an enlarged scale portions of spectra similar to those shown in FIGS. 14 and 15, respectively.
Figure 17:
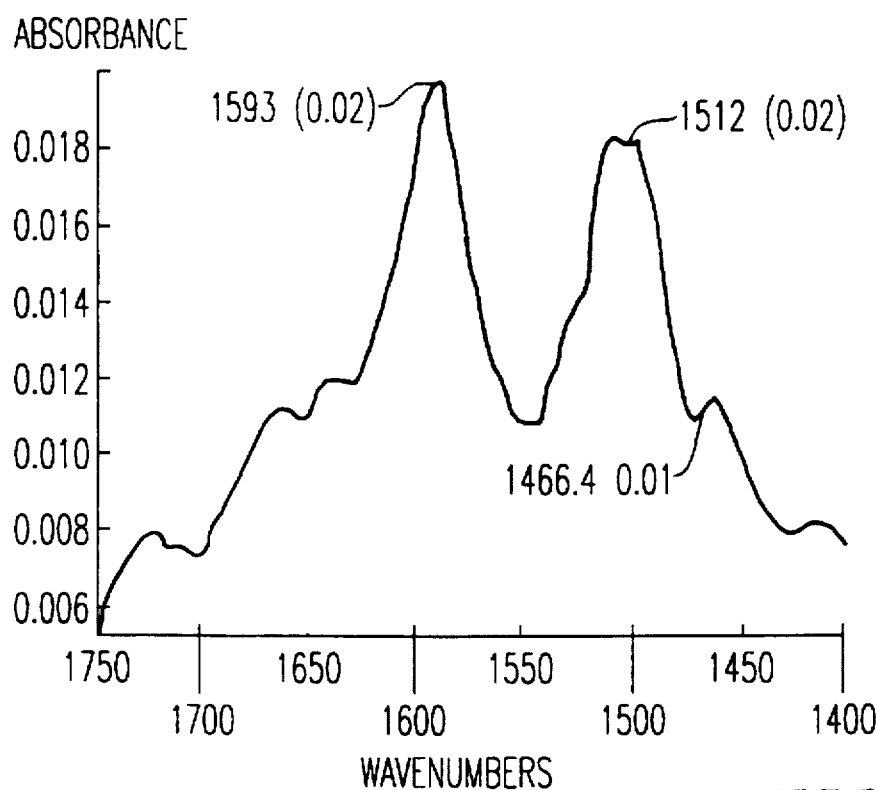

To assess whether a sample of polyaniline is "non-protonated" use can be made of infra-red absorption spectographs. FIG. 14 shows an infra-red spectrum of a sample of non-protonated emeraldine base form of polyaniline made in accordance with the method of the invention, while FIG. 15 shows an infrared spectrum of slightly protonated (i.e. greater than 1%) polyaniline. In FIG. 15, towards the high energy end of the spectrum a large rising background is visable. This is due to a charge transfer band of emeraldine caused by the protonation. The extent of protonation can be determined by comparing the relative peak heights of the peaks in about the 1594 $cm^{-1}$ and 1512 $cm^{-1}$ band regions. In the case of the slightly protonated sample, see FIG. 17 where the peak in the 1594 $cm^{-1}$ band region is of higher intensity. In the case of the "non-protonated" sample, it is the peak in the 1512 $cm^{-1}$ band region which is of higher intensity, albeit shifted slightly in energy—see FIG. 16 and the shift from about 1512 $cm^{-1}$ to about 1501 $cm^{-1}$. The present inventors used this kind of data to estimate that the degree of protonation of the samples of "non-protonated" polyaniline was less than 1%.

It will be understood that the non-protonated polyaniline film or layer may be incorporated into gas sensor arrangements other than those based on a pair of interdigitated electrodes, e.g. as shown in FIG. 1. For example, it is known that gas sensors can be based on charge-flow transistors (CFT), in which case a thin film of an electrically-resistive gas sensing polymer material is deposited e.g. by spin coating, in a 'gap' or 'hole' deliberately provided in the gate electrode of the CFT. The presence of the thin film of resistive material in the 'hole' in the gate structure results in there being a time delay between the application of the gate-to-source voltage and the appearance of a complete channel. The time delay is dependent on the resistivity of the thin film. It will be appreciated that the resistivity of the film is affected by the gas or gases in the immediate vicinity of the film and that such a response can be used as the basis for sensing gas.

Applicants have used spin-coating to fill such a 'gap' or 'hole' in a CFT to produce a film of non-protonated polyaniline approximately 100 nm thick; the 'hole' being 35 μm (microns) in diameter. By way of illustration only, in the presence of 4 ppm NOx, it was found that the turn on time of this modified CFT was substantially decreased, resulting in a changed drain-source current ($I_{DS}$) versus time response as compared with that obtained in the presence of a reference atmosphere of nitrogen.

It is again envisaged that by initially employing known concentrations of a gas, the measurements can be used to calibrate the sensor. Thus, when an unknown concentration of gas is sampled, the measurements obtained can be used to determine the concentration of the sampled gas.

We claim:

1. A gas sensor comprising a film or layer of non-protonated polyaniline as the gas sensing material, in which the non-protonated polyaniline is in the base emeraldine form having the formula:

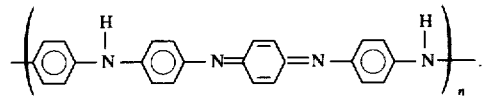

2. A gas sensor comprising a film or layer of non-protonated polyaniline as the gas sensing material, in which the non-protonated polyaniline is in the base leuco-emeraldine form having the formula:

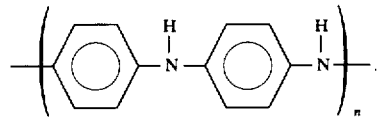

3. A gas sensor as claimed in claim 1, in which the film or layer of non-protonated polyaniline is deposited on a substrate which supports spaced electrodes, with the film or layer bridging the spaced electrodes.

* * * * *